United States Patent [19]
Stetler-Stevenson et al.

[11] Patent Number: 5,698,671
[45] Date of Patent: Dec. 16, 1997

[54] METALLOPROTEINASE PEPTIDES

[75] Inventors: William G. Stetler-Stevenson, Gaithersburg; Lance A. Liotta, Potomac; Henry C. Krutzsch, Bethesda, all of Md.

[73] Assignee: The United States of America as represented by the Secretary of the Department of Health and Human Services, Washington, D.C.

[21] Appl. No.: 284,721

[22] Filed: Aug. 2, 1994

Related U.S. Application Data

[63] Continuation of Ser. No. 75,855, Jun. 10, 1993, abandoned, which is a continuation of Ser. No. 837,102, Feb. 19, 1993, abandoned, which is a continuation of Ser. No. 326,334, Mar. 21, 1989, abandoned.

[51] Int. Cl.$^6$ ..................................................... C07K 7/00
[52] U.S. Cl. ........................... 530/324; 530/325; 530/327; 425/40; 425/489; 514/12
[58] Field of Search .......................... 530/324, 350, 530/325, 327; 514/12; 435/69.2; 424/40, 489

[56] References Cited

PUBLICATIONS

Carmichael, DF et al. "Primary Structure and cDNA Cloning of Human Fibroblast Collagenase Inhibitor", Proc. Natl. Acad. Sci., USA vol. 83 pp. 2407–2411 (Apr. 1986).

Article entitled "Cancer Metastasis and Angiogenesis: An Imbalane of Positive and Negative Regulation" by Liotta Lance A. et al. Cell vol. 64, pp. 327–336 Jan. 25, 1991.

Article entitled "Inhibition of In Vitro Tumor Cell Invasion by Arg–Gly–Asp–containing Synthetic Peptides" by Kurt R. Gehlsen, et al. The Journal of Cell Biology, vol. 106, Mar. 1988 pp. 925–930.

Article entitled "YIGSR, a synthetic Laminin Pentapeptide, Inhibits Experimental Metastasis Formation" by Yukihide Iwamoto, et al. Science, vol. 238 pp. 1132–1134 Nov. 1987.

Article entitled "Inhibition of Human Renin by Synthetic Peptides Derived from Its Prosegment" by Frederic Cumin et al. The Journal of Biological Chemistry vol. 260 No. 16, pp. 9154–9157.

Article entitled "Potent new inhibitors of human renin"Nature vol. 299 Oct. 7, 1982 by M.Szelke et al.pp.555–557.

Article entitled "Inhibition of Human Type IV Collagenase by a Highly Consvd . . . "by Stetler–Stevenson et al(NIH).

Article entitled "Preferential Inhibition of 72 kDa and 92kDa Gelatinases by TIMP–2" by Eric W. Howard et al. submitted to Journal of Biological Chemistry No. 1, 1990 revised Mar. 12, 1991.

*Primary Examiner*—Christine M. Nucker
*Assistant Examiner*—Laurie Scheiner
*Attorney, Agent, or Firm*—Townsned and Townsend and Crew LLP

[57] ABSTRACT

Inappropriate degradation of extracellular matrix molecules by metalloproteinases plays an important role in a wide variety of pathologic conditions including neoplasia and arthritis. The present invention is an isolated protein of approximately 23,000 daltons in size which binds to metalloproteinases with high affinity, can be purified using affinity chromatography on solid phase metalloproteinases, and is potentially useful for therapy of pathologic conditions involving the inappropriate production of metalloproteinases. This protein is characterized by the presence of the following amino acid sequences:
C S C S P V H P Q Q A F C N A D V V I - RAKAVSEKEVDSGNPIYGNNI KDIEFIYTAPSEAVCGVELDVEGK
K R H I T L C D F I V P W D T L S T T Q K K S L N - HRYQQGCEECKITRCPMIPCYISSPDECLWTDTVV KFFACIKRHITLCDFIVPWSQIADXLSS With the positions of the cysteine residues and associated disulfide bridges required for biologic activity.

9 Claims, 2 Drawing Sheets

Upper row: Previously known sequence of human tissue inhibitor of metalloproteinase (TIMP)
Lower row: Novel sequence of invention indicating scattered short homologies to TIMP and conservation of cysteines

METALLOPROTEINASE PEPTIDES

This is a Continuation of application of Ser. No. 08/075,855, filed Jun. 10, 1993, now abandoned, which is a continuation of application Ser. No. 07/837,102 filed Feb. 19, 1992, now abandoned, which is a continuation of application Ser. No. 07/326,334, filed on Mar. 21, 1989, now abandoned.

FIELD OF THE INVENTION

The invention relates to isolated proteins or peptides useful in metalloproteinase inhibition. Specifically, the invention relates to a novel protein, isolated from the conditioned media of cultured human tumor cells which binds with high affinity to metalloproteinase enzymes and analogs thereof. The natural protein is defined by the presence of specific cysteine-containing amino acid sequences. The invention further relates to a novel means of purifying metalloproteinase inhibitors using metalloproteinase affinity chromatography.

BACKGROUND OF THE INVENTION

Matrix metalloproteinases are a family of neutral metalloenzymes capable of degrading extracellular matrix macromolecules. All require a metal ion (calcium and/or zinc) for hydrolytic activity, and all are secreted in the latent pre-enzyme form. Members of this family which have been isolated and characterized include interstitial fibroblast collagenase, stromelysin, and type IV collagenase. Other potential members include a poorly characterized 94,000 dalton gelatinase and several low molecular weight gelatinases and telopeptidases.

The matrix metalloproteinases are thought to play an important role in disease processes characterized by the inappropriate destruction of the extracellular matrix. These diseases include inflammatory processes such as rheumatoid arthritis and other autoimmune disorders, tumor cell invasion and metastases formation, and corneal ulceration. Many tissues contain natural inhibitors of the matrix metalloproteinases. In many cases, this inhibitory activity is derived from the antiproteases in plasma, particularly $\alpha_2$-macroglobulin and $\beta_1$-anticollagenase. $\alpha_2$-Macroglobulin is a high molecular weight (725,000) inhibitor present in serum. It is thought to account for 95% of the collagenolytic inhibitory activity present in serum. Because of its large size, it is normally unable to pass the vascular permeability barrier under conditions of extreme inflammation in which there is increased capillary permeability, $\alpha_2$-macroglobulin may enter the tissue compartment and play a role in the regulation of matrix metalloproteinases. The mechanism of inhibition of the matrix metalloproteinases by $\alpha_2$-macroglobulin has not been directly studied. However, it is thought to be similar to the mechanism that causes inhibition of other proteases. Hence, the mechanism is not believed to be unique for the matrix metalloproteinases.

$\beta_1$-Anticollagenase is approximately 40,000 daltons in size. It accounts for approximately 5% of the metalloproteinase inhibiting activity of serum. This inhibitor is thought to pass the vascular permeability barrier and be widely distributed in the tissue compartments. $\beta_1$-Anticollagenase may be related to another group of natural inhibitors of the matrix metalloproteinases referred to as TIMPs, tissue inhibitors of metalloproteinase.

TIMP is a 28,000 dalton protein which was originally isolated from rabbit bone culture and has subsequently been identified in human connective tissues, serum and amniotic fluid (Welgus and Stricklin, 1983, J. Biol. Chem. 258: 12259–12264). This inhibitor is a glycoprotein and specifically inhibits interstitial collagenase on a 1:1 stoichiometric basis. Reduction and alkylation of TIMP abolishes all inhibitory activity. Reduction of TIMP mRNA levels has been associated with the acquisition of the metastatic phenotype in previously nonmetastatic cell lines (Khokha et al., 1989, Science 243: 947–950). Another class of biologically active collagenase inhibitors is composed of low molecular weight (>10,000 daltons) cationic proteins isolated from cartilage aorta and teeth, but which are poorly characterized.

DESCRIPTION OF FIGURES

FIG. 2: Sequence of human Tumor Cell Collagenase Inhibitor (TCCI) and Homology to Tissue Inhibitors of Metalloproteinase (TIMP). The bottom line shows the novel sequence of the invention obtained from direct amino acid sequencing of the protein and endoproteinase Lys-C peptides. The sequence information obtained is aligned (top line) with the known sequence of TIMP to demonstrate scattered homology and conservation of the cysteine residues. The novel sequences of the TCCI indicate that it is a product of a separate gene distinct from the gene which encodes TIMP.

SUMMARY OF THE INVENTION

It is the object of this invention to provide means of purifying natural inhibitors of metalloproteinase.

It is a further object of this invention to provide metalloproteinase inhibitors and derivatives thereof. The inhibitors may be obtained from natural sources, may be produced by synthetic means such as the Merrifield process, or by genetically engineered organisms or cell lines. The inhibitors of the invention may be used to treat disease conditions which result from activity of metalloproteases. Furthermore, since metalloprotease activity is essential to the implantation of the Zygote, these inhibitors are useful as contraceptives.

The present invention is a isolated novel metalloproteinase inhibitor distinct from previous inhibitors mentioned above. The invention is a novel protein of approximately 23,000 daltons which binds to metalloproteinases and can be isolated using affinity chromatography on solid phase purified metalloproteinases. The amino acid sequence of the isolated protein shows that it is a new gene product not previously discovered and has areas of sequence homology with the known natural tissue inhibitor of metalloproteinases (TIMP).

DETAILED DESCRIPTION OF THE INVENTION

A new inhibitor was discovered in serum-conditioned media of a human A2058 melanoma cell line. This cell line is available from the American Tissue Culture Collection. The inhibitor was isolated and purified by means described below. It was discovered that the metalloprotease inhibitor of the invention contained a unique amino acid sequence but also contained a cysteine residue at the same intervals as the previously described tissue inhibitor of metalloproteinase protein (TIMP) previously described in European patent 189,784. Analogs of the natural inhibitor of the invention can be made by preparing peptides and proteins having cysteines at the same intervals as the cysteines in the natural inhibitor. Other amino acids may vary from the pattern of the natural inhibitor so long as the cysteine is located at the appropriate intervals. At least two appropriately spaced cysteines must be present in the peptide to ensure inhibitory activity by virtue of a disulfide bridge formation.

The fragments derived from the natural TCCI molecule were used as immunogens. Antibodies to the fragments can be used to detect the natural inhibitor in serum.

Particularly preferred peptides are those having at least 3 cysteines. An amino acid sequence containing the sequence CSCSPVHPQQAFCNA derived from the amino terminal of the molecule and a segment containing the amino acid sequence CPMIPCYISSPDECLWTDTVVKFFAC appear particularly active.

EXAMPLE 1

Figure 1A:
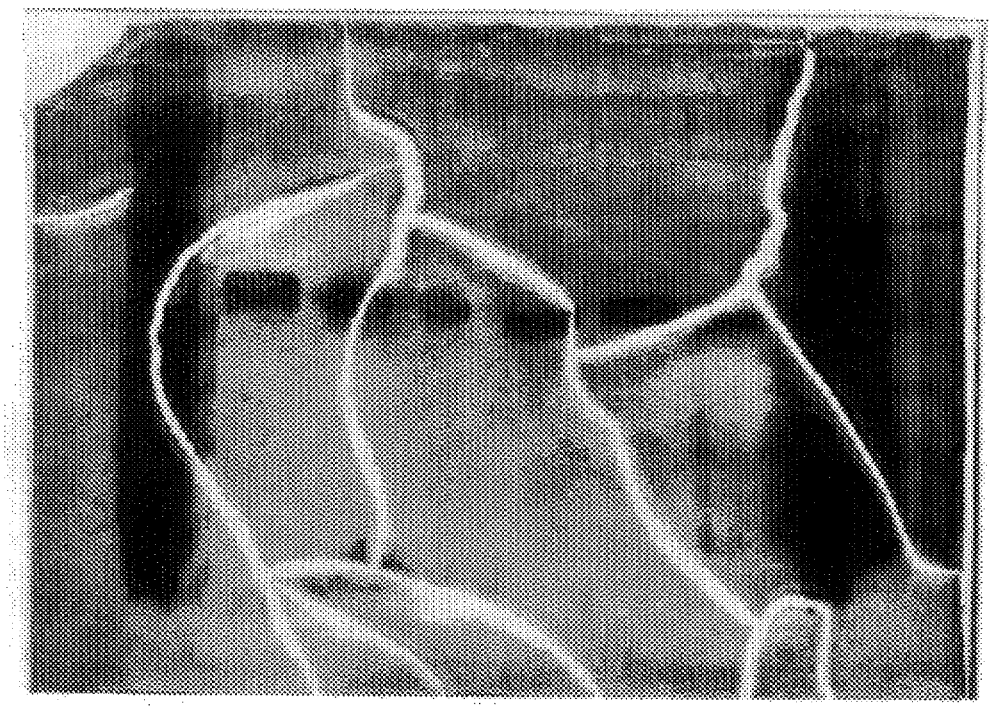
FIG. 1: Gel Electrophoresis of Purified Tumor Cell Collagenase Inhibitor. Tumor cell collagenase inhibitor was purified by affinity chromatography of A2058 human melanoma cell conditioned media on type IV collagenase-gelatin sepharose, as shown in FIG. 1A. The material eluted from this column was then further purified by reverse phase high performance liquid chromatography using a 0.45×10-cm RP 300 column (Pierce Chemical Co.), as shown in FIG. 1B. 10 μl of the tumor cell collagenase inhibitor peak was heated with sample buffer containing βmercaptoethanol before electrophoresis on a 15% acrylamide gel. Following electrophoresis, the sample was silver stained to visualize the proteins.
Figure 1B:
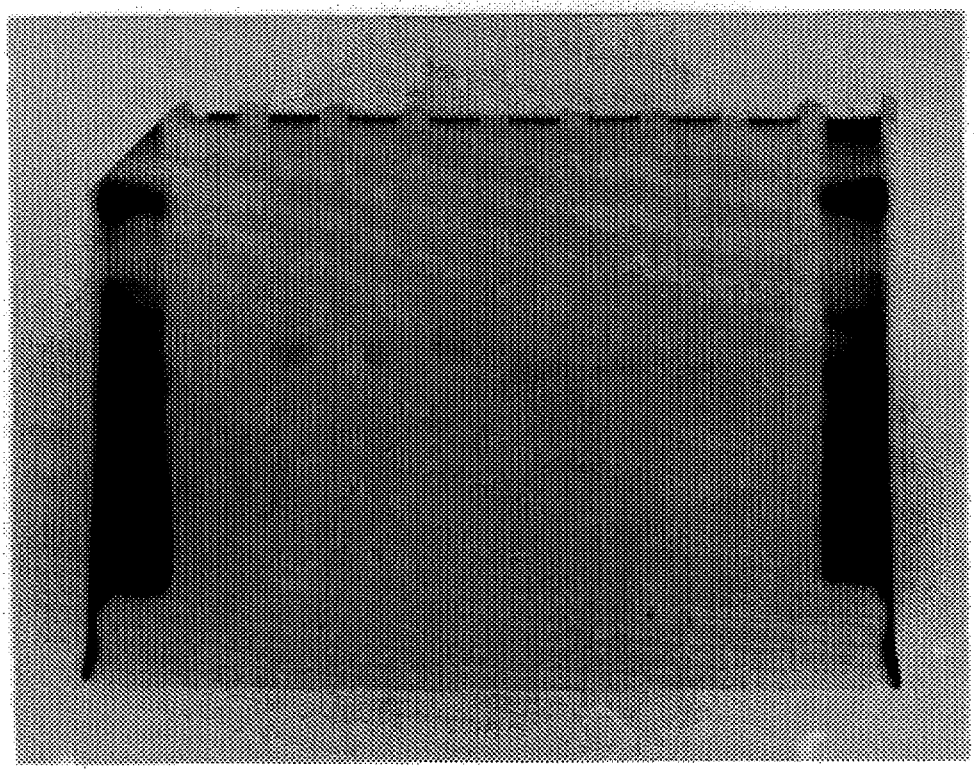

Tumor cell collagenase inhibitor (TCCI) was purified from the serum-free conditioned media of the human A2058 melanoma cell line. The media was collected, filter sterilized by passing through a 0.22μ filter, and stored frozen at −20° C. The media was thawed and concentrated over a YM 30 ultrafiltration membrane (Amicon Co.) at 4° C. The concentrated conditioned media was passed through a gelatin sepharose affinity column (1×10 cm) previously equilibrated in 0.5M NaCl, 0.05M Tris HCl, 0.01M CaCl$_2$, 0.02% Brij 35, pH 7.5. After loading, the column was washed exhaustively with this same buffer. The column was then eluted using 0.5M NaCl, 0.05M Tris HCl, 0.01M CaCl$_2$, 0.02% Brij 35, 10% dimethyl sulfoxide, pH 7.5. The eluted material was rapidly concentrated and the buffer exchanged for 0.15M NaCl, 0.05M Tris HCl, 0.01M CaCl$_2$, pH 7.5 by ultrafiltration using a YM 30 membrane (Amicon). This material was aliquoted and stored frozen at −70° C. Further purification was achieved by reverse phase chromatography over a 0.45×10 cm RP 300 column (Pierce Chemical Co.) equilibrated in 0.1% trifluoroacetic acid. The column was eluted with a linear gradient to 60% acetonitrile. When this material was electrophoresed under reducing conditions on a 15% acrylamide gel, a single band of protein was identified with an apparent molecular weight of 23,000 daltons, purified TCCI (see FIG. 1).

EXAMPLE 2

The purified TCCI material was subjected to direct amino acid sequencing following reduction and alkylation (Stetler-Stevenson et al., 1989, J. Biol. Chem. 264: 1353–1356, 1989). This yielded the unique amino terminal amino acids (peptide 1–40) of TCCI which are shown in FIG. 2.

EXAMPLE 3

The purified TCCI was also treated with endoproteinase Lys-C to generate a limited proteolytic digest. These TCCI peptides were again purified by reverse phase chromatography prior to amino acid sequencing. Additional unique sequences obtained from the peptides 56–79, 93–152 and 162–196 are also shown in FIG. 2.

These data show that while TCCI shows scattered homology with TIMP, particularly with respect to the conservation of the position of the cysteine residues, all of the TCCI peptides are distinctly different from TIMP. Thus, the peptides of the invention are encoded by a gene different from that which encodes TIMP. This demonstrates that TCCI is the product of a separate gene. Synthetic peptides were prepared using the sequence from the amino terminal portion of the TCCI molecule. These were coupled to bovine serum albumin for use in generating anti-peptide antibodies by standard methods. The antibodies were affinity purified using solid phase peptide-affinity chromatography as previously described (Stetler-Stevenson et al., 1989, J. Biol. Chem. 264: 1353–1356, 1989). These antibodies are reactive on standard western and immunoblots.

The isolated, purified TCCI and analogs can be used therapeutically in those diseases characterized by the uncontrolled activity of matrix metalloproteinases. Such diseases include arthritis diabetes, cancer, ulcers of mucosa and epithelial tissues, autoimmune mediated inflammation, lung injury, granulomatous diseases. Other therapeutic benefit might also be obtained in diseases with basement membrane destruction such as lupus, autoimmune neural disorders, myocyte destruction such as myodystrophies, myocardial infarct and glomerulopathies. TCCI could also be used as a potential birth control methodology by preventing embryo/placental attachment or invasion.

When metalloproteinase inhibitors of the invention are used in the treatment of inappropriate angiogenesis, arthritis, tumor growth, invasion and metastasis, and granulomatous inflammatory conditions such as sarcoidosis and other pathological conditions, it is possible to estimate the amount of enzyme produced and the amount of peptide inhibitor required to inhibit greater than 90% of the active enzyme. For use in treating any disease condition, the therapeutic dose of the inhibitory peptide falls within an acceptable pharmacologic range of 1–250 mg/kg/da, with a more preferred dosage being 25–100 mg/kg/d. The dosage for a given patient will depend on the amount of enzyme produced in the patient, the condition and size of the patient. The inhibitors may be given as infusions or by any means which provides ready transmission into the circulation. Lyophilized powders may be "snorted". Preparations for buccal or sublingual administration may also be given. For respiratory tract involvement, the peptides may be administered by inhalation. Aerosols are particularly useful for this purpose. For conditions of the eye, the peptides may be administered as eye drops.

The isolated TCCI proteins, natural or recombinant, or active peptides derived therefrom can be administered intravenously, orally, intrauterine, by inhalation or topical application. For example, a topical application can be prepared using a suitable carrier for treatment of basal cell carcinomas or melanomas of the skin or for the treatment of corneal ulceration.

The complete TCCI protein or TCCI peptides can be produced by purification from natural sources, by synthetic peptide chemistry methods, or by recombinant DNA technology. In the latter case, suitable cDNA clones for TCCI in a suitable expression vector can be used to produce peptides with TCCI activity.

TCCI peptides and antibodies to TCCI are also useful in diagnosis of diseases characterized by abnormal balances of metalloproteinase/inhibitor ratios. Purified TCCI may be used by virtue of its ability to bind metalloproteinases as a means to purify and or detect metalloproteinases from any natural source. Suitable immunoassays for TCCI could include anti-TCCI antibodies, reference TCCI antigen and solid or solution phase reactions. Purified TCCI or peptide domains of TCCI can be tagged with suitable enzymatic, fluorescent or radioactive labels by means well known in the art.

We claim:

1. A peptide derivable from TCCI having the amino acid sequence:
   (i) CSCSPVHPQQAFCNADVVIRAKAVSEKEVDSGNPIYGNNI
   (ii) KDIEFIYTAPSEAVCGVELDVEGK
   (iii) KRHITLCDFIVPWDTLSTTQKKSLNHRYQQGCEECKITRCPMIPCYISSPDECLWTDTVV or
   (iv) KFFACIKRHITLCDFIVPWSQIADXLSS.

2. A peptide of claim 1 of the structure CSCSPVHPQQAFC.

3. A peptide of claim 1 consisting of the amino acid sequence CSCSPVHPQQAFCNADVVIRAKAVSEKEVDSGNPIYGNNI.

4. A therapeutic preparation consisting of the isolated protein or peptides of claim 1 suspended in a pharmaceutically acceptable carrier.

5. A composition of matter which is a powder containing at least one peptide of claim 1.

6. A composition of matter which is at least one peptide of claim 1 in a carrier.

7. A composition of matter of claim 6 containing an adjuvant.

8. A composition of claim 6 which is an aerosol.

9. A composition of claim 6 which is a pellet suitable for intrauterine implantation.

* * * * *